United States Patent [19]

Clemence et al.

[11] Patent Number: 5,278,180
[45] Date of Patent: * Jan. 11, 1994

[54] 4,5-BIS(ARYL) 4H-1,2,4-TRIAZOLES DERIVATIVES AND ANALGESIC USE

[75] Inventors: François Clemence, Paris; Claudine Maushart, Le Raincy; Philippe Mackiewicz, Livry-Gargan; Françoise Delevallee, Fontenay-Sous-Bois, all of France

[73] Assignee: Roussel Uclaf, France

[*] Notice: The portion of the term of this patent subsequent to Apr. 23, 2002 has been disclaimed.

[21] Appl. No.: 863,801

[22] Filed: May 4, 1992

Related U.S. Application Data

[63] Continuation of Ser. No. 561,122, Jul. 30, 1990, abandoned, which is a continuation of Ser. No. 778,566, Sep. 20, 1985, abandoned.

[30] Foreign Application Priority Data

Sep. 24, 1984 [FR] France ................... 84 14598

[51] Int. Cl.$^5$ ..................... A61K 31/41; C07D 249/08
[52] U.S. Cl. ................... 514/383; 548/267.2; 548/267.8; 548/268.6
[58] Field of Search .............. 548/267.2, 267.8, 268.6; 514/383

[56] References Cited

U.S. PATENT DOCUMENTS 4,512,997  4/1985  Meier et al. ................... 514/383

OTHER PUBLICATIONS

Reimlinger et al, "Cyclocondensation of open-chain, etc." CA 74: 87898y (1971).
Roussel-Uclaf, "4H-1,2,4-Triazole derivatives, etc" CA 97: 92286b (1982).

*Primary Examiner*—Patricia L. Morris
*Attorney, Agent, or Firm*—Bierman & Muserlian

[57] ABSTRACT

A novel process for the preparation of 4H-1,2,4-triazoles in their racemic or optically active forms of the formula

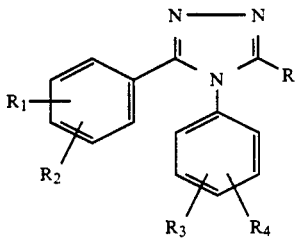

wherein the compounds have analgesic activity.

15 Claims, No Drawings

4,5-BIS(ARYL) 4H-1,2,4-TRIAZOLES DERIVATIVES AND ANALGESIC USE

PRIOR APPLICATION

This application is a continuation of U.S. patent application Ser. No. 561,122 filed Jul. 30, 1990 which is a continuation of U.S. patent application Ser. No. 778,566 filed Sep. 20, 1985, both now abandoned.

STATE OF THE ART

Commonly assigned U.S. Pat. No. 4,512,997 describes 4H-1,2,4-triazoles substituted in the 3-position with hydrogen, alkyl of 1 to 4 carbon atoms, —CH$_2$COOH and —CH$_2$COOAlk having analgesic activity.

OBJECTS OF THE INVENTION

It is an object of the invention to provide a novel process for the preparation of 4H-1,2,4-triazoles of formula I and their non-toxic, pharmaceutically acceptable acid addition salts and novel intermediates.

It is another object of the invention to provide novel compounds of formula I and their non-toxic, pharmaceutically acceptable acid addition salts wherein

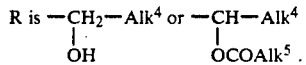

It is a further object of the invention to provide novel analgesic compositions and a novel method of relieving pain in warm-blooded animals.

These and other objects and advantages of the invention will become obvious from the following detailed description.

THE INVENTION

The novel process of the invention for the preparation of 4H-1,2,4-triazoles in their racemic or optically active forms of the formula

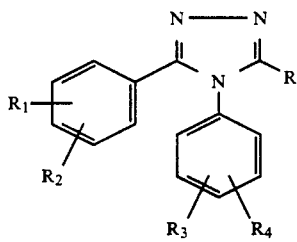

wherein $R_1$, $R_2$, $R_3$ and $R_4$ are in any position on the benzene nuclei and are individually selected from the group consisting of hydrogen, —OH, alkyl and alkoxy of 1 to 4 carbon atoms, —NH$_2$, —CF$_3$, halogen, —NO$_2$, —NH—Alk$^1$ and

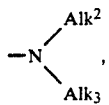

Alk$^1$, Alk$^2$ and Alk$^3$ being individually alkyl of 1 to 4 carbon atoms or $R_1$ and $R_2$ or $R_3$ and $R_4$ together form methylenedioxy and R is selected from the group consisting of alkyl of 1 to 4 carbon atoms, —CHOH—Alk$^4$ and

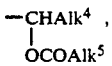

Alk$^4$ and Alk$^5$ individually being alkyl of 1 to 5 carbon atoms and their acid addition salts comprising reacting a compound of the formula

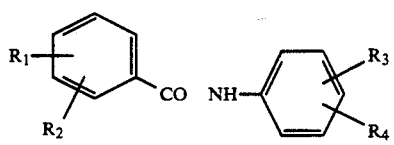

wherein $R_1$, $R_2$, $R_3$ and $R_4$ have the above definitions with a chlorinating agent to obtain an imidoyl chloride of the formula

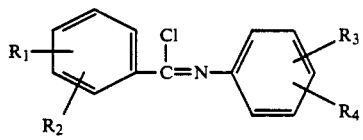

reacting the latter with a racemate or optically active isomer of a hydrazide of the formula

wherein Z is selected from the group consisting of alkyl of 1 to 4 carbon atoms and

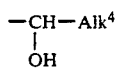

wherein Alk$^4$ has the above definition to obtain a racemate or optically active isomer of a compound of the formula

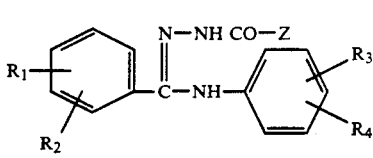

heating the latter to cyclize the same to obtain a compound of formula I in racemic or optically active form wherein R is alkyl of 1 to 4 carbon atoms or

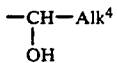

and optionally esterifing the latter to obtain a compound of formula I wherein R is

and optionally forming the acid addition salts thereof.

Examples of $R_1$, $R_2$, $R_3$ and $R_4$ as alkyl are methyl, ethyl, n-propyl, isopropyl and n-butyl and as halogen are fluorine, chlorine, bromine or iodine, preferably chlorine or bromine. Examples of $Alk^1$, $Alk^2$, $Alk^3$ and $Alk^4$ are methyl, ethyl, n-propyl, isopropyl and n-butyl.

Examples of acids to form the non-toxic, pharmaceutically acceptable acid addition salts are inorganic acids such as hydrochloric acid, hydrobromic acid, sulfuric acid and phosphoric acid and organic acids such as acetic acid, propionic and maleic acid, hemisuccinic acid. etc.

In a preferred mode of the process of the invention, the starting compound of formula II has one of $R_1$ and $R_2$ as hydrogen and the other is p-methoxy, p-nitro or

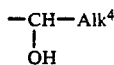

and one of $R_3$ and $R_4$ is hydrogen and the other is p-methoxy, p-$NO_2$ or p-dimethylamino and in the hydrazide of formula IV, Z is ethyl or —CH—$Alk^4$
|
OH and $Alk^4$ is alkyl of 1 to 4 carbon atoms in racemic or optically active form. If $R_1$ or $R_2$ and/or $R_3$ or $R_4$ is p-nitro, the compounds can be converted into the corresponding compounds where the p-nitro is converted into the p-dimethylamino.

The compounds of formula I contain at least one asymmetic carbon atoms to have racemic or optically active forms.

The novel 4H-1,2,4-triazoles of the invention are racemates or optically active isomers of compounds of the formula

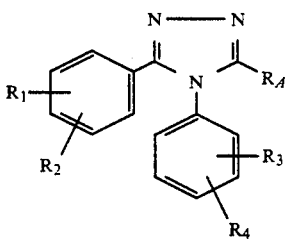

IA wherein $R_1$, $R_2$, $R_3$ and $R_4$ have the above definitions and $R_A$ is selected from the group consisting of

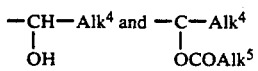

and $Alk^4$ and $Alk^5$ are individually alkyl of 1 to 4 carbon atoms and their non-toxic, pharmaceutically acceptable acid addition salts.

Among the preferred compounds of formula IA are those wherein one of $R_1$ and $R_2$ is hydrogen and the other is p-methoxy or p-dimethylamino and those wherein one of $R_3$ and $R_4$ is hydrogen and the other is p-methoxy or p-dimethylamino and their non-toxic, pharmaceutically acceptable acid addition salts in their racemic or optically active form. Especially preferred is 5-[4-(dimethylamino)-phenyl]-4-(4-methoxyphenyl)-α- methyl-4H-1,2,4-triazole-3-methanol in racemic and optically active form and its non-toxic, pharmaceutically acid addition salts.

The products of formula I wherein R is other than $R_A$ have already been claimed in U.S. Pat. No. 4,512,997 and are prepared by reacting a compound of the formula

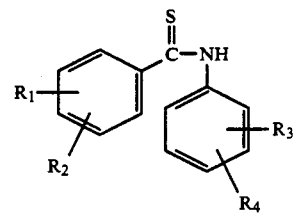

III' with hydrazine to obtain a compound of the formula

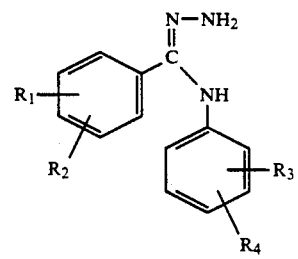

IV' which is reacted with an acid or of a functional derivative of an acid of the formula $XCO_2H$ wherein X is alkyl of 1 to 4 carbon atoms to obtain a compound of the formula

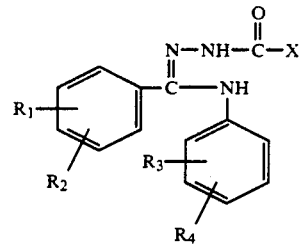

V' which is cyclized by heating to obtain the compound of formula I in which $R_1$, $R_2$, $R_3$ and $R_4$ are defined as above and R is alkyl of 1 to 4 carbon atoms.

In this process, the intermediate amidrazone IV' obtained is unstable and impurities, particularly tetrazines, form during the synthesis. The formation of these degradation products makes the purification of the amidrazone and of the acylamidrazone V' formed thereafter difficult. In the process of the present invention, no unstable intermediates are formed and the acylamidrazone of formula V' is easily obtained since it is stable, free of impurities and easily purified.

In a preferred mode of the process of the invention, the chlorinating agent to form the imidoyl chloride of formula III is preferably thionyl chloride or phosgene but other agents such as phosphorus pentachloride or phosphorus oxychloride may be used. The reaction may be carried out in the absence of a solvent by refluxing in the chlorinating agent. A suitable solvent is toluene, benzene or dichloromethane if one is to be used. When one of $R_1$, $R_2$, $R_3$, or $R_4$ contains a sensitive group such as $$-N\begin{matrix}Alk^2\\ Alk^3\end{matrix}$$

the preferred chlorinating agent is phosgene and the reaction is effected at $-30°$ to $-60°$ C. in the presence of a tertiary base such as pyridine or triethylamine to react with the hydrogen chloride formed.

The condensation of the compounds of formulae III and IV is preferably in a solvent such as toluene or benzene at reflux. The esterification to obtain a compound of formula I when R is $$-\underset{\underset{OCOAlk^5}{|}}{CH}-Alk^4$$

is effected under known conditions.

The compounds of formula I are useful intermediates and can be converted by known reactions such as esterification or etherification of the hydroxyl group or conversion of an alkoxy into hydroxyl, a nitro group into $-NH_2$ or $-N(alkyl)_2$; etc.

The novel analgesic compositions of the invention are comprised of an analgesically effective amount of at least one compound of formula $I_A$ and their non-toxic, pharmaceutically acceptable acid addition salts in racemic or optically active form and an inert pharmaceutical carrier or excipient. The compositions may be in the form of tablets, dragees, capsules, granules, suppositories, ointments, creams, gels, injectable solutions or suspensions and aerosol preparations.

Examples of suitable excipients are talc, gum arabic, lactose, starch, magnesium stearate, cocoa butter, aqueous and non-aqueous vehicles, fatty substances of animal or vegetable origin, paraffinic derivatives, glycols, diverse wetting agents, dispersants and emulsifiers and preservatives.

Among the preferred compositions of the invention are those with compounds of formula I wherein one of $R_1$ and $R_2$ is hydrogen and the other is p-methoxy or p-dimethylamino and those wherein one of $R_3$ and $R_4$ is hydrogen and the other is p-methoxy or p-dimethylamino and their non-toxic, pharmaceutically acceptable acid addition salts in their racemic or optically active form. Particularly preferred are compositions containing 5-[4-(dimethylamino)-phenyl]-4-(4-methoxyphenyl)-α-methyl-4H-1,2,4-triazole-3-methanol and its non-toxic, pharmaceutically acceptable acid addition salts in racemic or optically active form since it also possesses anti-inflammatory activity useful in cases of chronic inflammation.

The compositions of the invention are useful for the treatment of muscular, articular or nervous pains, of rheumatic affections, of dental pain, of shingles and migraines and as a complementary treatment in infections and febrile states. Compositions containing 5-[4-dimethylamino)-phenyl]-4-(4-methoxyphenyl)-α-methyl-4H-1,2,4-triazole-3-methanol are useful for the treatment of degenerative inflammatory diseases such as osteoarthrosis, various collagenoses (tendinitis, etc.) rheumatismal diseases, rheumatic polyarthritis, enkylosing spondylarthritis, as well as in the treatment of other diseases of auto-immune nature such as disseminated erythrematous lupus, glomerulonephritis, multiple sclerosis.

The novel method of the invention of relieving pain in warm-blooded animals, including humans, comprises administering to warm-blooded animals an analgesically effective amount of at least one compound of formula $I_A$ and its non-toxic, pharmaceutically acceptable acid addition salts in racemic or optically active form. The compounds may be administered orally, rectally, parenterally or topically to the skin or mucosa. The usual daily dose will vary depending on the specific compound, condition treated and method of administration. For example, the compound may be orally administered at 0.30 to 30 mg/kg per day in the adult.

The compounds of formula II are described and prepared in U.S. Pat. No. 4,512,997 and the compounds of formula IV may be prepared by reacting a compound of the formula $$CH_3O-\overset{\overset{O}{\|}}{C}-R \text{ or } CH_3-CH_2-O-\overset{\overset{O}{\|}}{C}-R$$

with hydrazine hydrate.

The compounds of formula III are novel intermediates except for N-(4-methoxyphenyl)-4-nitrobenzenecarboximidoyl chloride and N-(4-methoxyphenyl)-4-methoxybenzene-carboximoyl chloride.

In the following examples there are described several preferred embodiments to illustrate the invention. However, it should be understood that the invention is not intended to be limited to the preferred embodiments.

EXAMPLE 1

3-ethyl-4-(4-methoxyphenyl)-5-(4-nitrophenyl)-4H-1,2,4-triazole

STEP A: N-(4-methoxyphenyl)-4-nitrobenzamide 12.3 g of p-anisidine were added in small fractions to a suspension of 18.6 g of 4-nitrobenzoic acid chloride in 100 ml of pyridine and the mixture was heated for 2 hours at reflux. After returning to ambient temperature, the solution was poured into 500 ml of iced water and the precipitate formed was separated and washed with water, then dried under reduced pressure at 80° C. to obtain 20 g of N-(4-methoxyphenyl)-4-nitrobenzamide melting at 200° C.

STEP B: N-(4-methoxyphenyl)-4-nitrobenzene carboximidoyl chloride

A mixture of 1.36 g of N-(4-methoxyphenyl)-4-nitrobenzamide and 5 ml of thionyl chloride was refluxed for 6 hours and then 30 ml of benzene were added. The benzene and the thionyl chloride were eliminated under reduced pressure to obtain N-(4-methoxyphenyl)-4-nitrobenzene carboximide chloride melting at 120° to 122° C.

STEP C: Propionic acid hydrazide 38.83 ml of hydrazine hydrate and 52.42 g of ethyl propionate were refluxed for 18 hours to obtain propionic acid hydrazide with a boiling point of 100° C. at 6 mmHg.

STEP D: 2-(1-oxopropyl)-hydrazide of N-(4-methoxyphenyl)-4-nitrobenzene carboximic acid 2.8 mg of triethylamine were added to a solution of 1.76 g of propionic acid hydrazide in 80 ml of toluene and 2.87 g of the product of Step B were added all at once with stirring for 15 minutes. After separating and drying, the residue obtained was taken up in 100 ml of water and was extracted with methylene chloride. The organic phase was dried and concentrated to dryness to obtain 2.2 g of 2-(1-oxopropyl)-hydrazide of N-(4-methoxyphenyl)-4-nitrobenzene carboximic acid melting at 158° C.

STEP E:
3-ethyl-4-(4-methoxyphenyl)-5-(4-nitrophenyl)-4H-1,2,4-triazole 4.38 g of the product of Step D in 60 ml of toluene were refluxed for two hours and the toluene was evaporated. The residue was taken up in isopropyl oxide, and the solid obtained was crystallized from a mixture of isopropyl oxide and isopropanol (2-1) to obtain 3-ethyl-4-(4-methoxyphenyl)-5-(4-nitrophenyl)-4H-1,2,4-triazole melting at 174° C.

EXAMPLE 2
4-[5-ethyl-4-(4-methoxyphenyl)-4H-1,2,4-triazole-3-yl]-benzenamine 100 g of the product of Example 1 were mixed at ambient temperature with 500 ml of 2N hydrochloric acid with stirring and a partial solution and then a crystallization were obtained. 0.5 g of 0.5% platinum oxide was then added, and stirring was continued for 4 days at 35°-38° C. under an atmosphere of hydrogen. After filtering, washing with water, the mixture was made alkaline with a pH of 11 with sodium hydroxide. The mixture was stirred for 1 hour at 20°-25° C. and filtered. The product was washed with water and dried at 60° C. to obtain 90.75 g of crude product. The latter was purified by triturating at reflux in ethyl acetate to obtain 90.7 g of 4-[5-ethyl-4-(4-methoxyphenyl)-4H-1,2,4-triazole-3-yl]-benzenamine melting at 210° C.

EXAMPLE 3
4-[5-ethyl-4-(4-methoxyphenyl)-4H-1,2,4-triazol-3-yl]-N-methyl-benzenamine

STEP A:
N-[4-(5-ethyl-4-(methoxyphenyl)-4H-1,2,4-triazol-3-yl)-phenyl]-formamide 60 g of the product of Example 2 and 200 ml of formic acid were stirred for 16 hours at ambient temperature and then for 4 hours on a water-bath at 80° C. The excess formic acid was eliminated, 400 ml of water were added to the residue and sodium hydroxide was added until precipitation took place. After stirring for 30 minutes and filtration the product was washed with water and dried at 70° to 80° C. to obtain 63 g of crude product. The latter was purified by dissolving at reflux in 2 liters of ethanol, filtering hot, distilling off 1,200 ml of ethanol, cooling and freezing for 1 hour at 0° C. After separating and washing with ethanol, 49 g of N-[4-(5-ethyl-4-(methoxyphenyl)-4H-1,2,4-triazol-3-yl)-phenyl]-formamide melting at 250° C. were obtained.

STEP B:
4-[5-ethyl-4-(4-methoxyphenyl)-4H-1,2,4-triazol-3-yl]-N-methyl-benzenamine At ambient temperature, 30 g of the product of Step A were dissolved in 1,200 ml of tetrahydrofuran and the solution was cooled to 7° C. Then, 120 ml of 25% of diethyldihydroaluminate in toluene in 120 ml of tetrahydrofuran were added with stirring for 1 hour at 5°-7° C. After returning to ambient temperature, the mixture was stirred for 2 hours, then cooled again to 7° C. after which 120 ml of sodium hydroxide were added slowly with stirring. Then, the mixture was poured into a mixture of 3,600 ml of ethyl acetate and 600 ml of water. Aftering stirring, the aqueous phase was decanted, and the organic phase was washed with an aqueous solution of sodium hydroxide and then with sodium chloride. Each washing solution was extracted with ethyl acetate and the combined extracts were dried and concentrated to dryness to obtain 23.5 g of crude product which was purified by dissolving it at reflux in 220 ml of ethanol. By filtering hot, washing with refluxing ethanol, concentrating to 110 ml under ambient pressure, cooling, separating, washing with ethanol and drying at 60° C., 10.2 g of 4-[5-ethyl-4-(4-methoxyphenyl)-4H-1,2,4-triazol-3-yl]-N-methyl-benzenamine melting at 198.5° C. were obtained.

EXAMPLE 4
3-ethyl-4-(4-methoxyphenyl)-5-(4-nitro-3-methyl-phenyl)-4H-1,2,4-triazole

STEP A:
N-(4-methoxyphenyl)-4-nitro-3-methylbenzamide

Using the procedure of Step A of Example 1, 15.5 g of 4-nitrometatoluyl chloride and 9.56 g of p-amisidine were reacted in the presence of pyridine to obtain 16.7 g of N-(4-methoxyphenyl)-4-nitro-3-methylbenzamide.

STEP B:
N-(4-methoxyphenyl)-4-nitro-3-methylbenzene carboximidoyl chloride 14 g of N-(4-methoxyphenyl)-4-nitro-3-methyl benzamide in suspension in 70 ml of thionyl chloride were heated for 20 hours at reflux. The solvent was eliminated by entrainment with benzene, and after drying under reduced pressure at ambient temperature, 15 g of N-(4-methoxyphenyl)-4-nitro-3-methylbenzene carboximidoyl chloride melting towards 80° C. were obtained.

STEP C:
3-ethyl-4-(4-methoxyphenyl)-5-(4-nitro-3-methyl-phenyl)-4H-1,2,4-triazole 1.4 ml of triethylamine, then 3 g of the product of Step B were introduced into a solution of 1.76 g of propionic acid hydrazide in 160 ml of toluene, this latter having been brought to reflux and then cooled. After refluxing for 1 hour, the toluene was eliminated under reduced pressure and the residue was taken up in 50 ml of chloroform and 50 ml of water. The aqueous phase was extracted with chloroform and the organic extracts were dried and concentrated to obtain an oil which was purified by chromatography on silica and elution with ethyl acetate and cyclohexane (8-2) to obtain 3 g of 3-ethyl-4-(4-methoxyphenyl)-5-(4-nitro-3-methyl-phenyl)-4H-1,2,4-triazole in the form of an oil which had an Rf of 0.6 on thin film chromatography (eluent:-chloroformethanol 9-1).

EXAMPLE 5
N,N-dimethyl-4-[5-ethyl-4-(4-methoxyphenyl)-4H-1,2,4-triazol-3-yl]-2-methyl-benzenamine A mixture of 2.6 g of the product of Example 4, 13 ml of formic aldehyde and 5.2 g of powdered zinc was cooled to 5° C. and then 13 ml of pure acetic acid were slowly introduced. The temperature was allowed to return to the ambient, and after stirring for 20 hours and filtering, the zinc was washed with 25 ml of a mixture of acetic acid and water, 100 ml of methylene and 50 ml of water. The filtrate was decanted and the aqueous phase was extracted with methylene chloride. The organic phase was washed with water, dried and concentrated to obtain 3 g of an oil which was taken up in 20 ml of isopropyl ether, then cooled to −50° C., returned to ambient temperature, filtered and dried under reduced pressure at 60° C. to obtain 1.85 g of product which was crystallized twice from a mixture of ethyl acetate and isopropyl ether (4-6) to obtain 1.2 g of N,N-dimethyl-4-[5-ethyl-4-(4-methoxyphenyl)-4H-1,2,4-triazol-3-yl]-2-methyl-benzenamine melting at 131° C.

EXAMPLE 6

3-ethyl-4-(4-methoxyphenyl)-5-(3-nitrophenyl)-4H-1,2,4-triazole

STEP A:

N-(4-methoxyphenyl)3-nitrobenzene-carboximidoyl chloride

Using the procedure of Step A of Example 1, 13 g of N-(4-methoxyphenyl)-3-nitrobenzamide prepared as in Step A of Example 1 and melting at 170° C. and 40 ml of thionyl chloride were reacted at reflux for 12 hours to obtain 14.5 g of N-(4-methoxyphenyl)-3-nitrobenzene-carboximidoyl chloride melting at 108° C.

STEP B:

3-ethyl-4-(4-methoxyphenyl)-5-(3-nitrophenyl)-4H-1,2,4-triazole

Using the procedure of Step B of Example 4, 15 g of the product of Step A and 8.8 g of propionic acid hydrazide in 200 ml of toluene and 14 ml of triethylamine were reacted to obtain 9.5 g of 3-ethyl-4-(4-methoxyphenyl)-5-(3-nitrophenyl)-4H-1,2,4-triazole melting at 126° C.

EXAMPLE 7

N,N-dimethyl-3-[5-ethyl-4-(4-methoxyphenyl)-4H-1,2,4-triazol-3-yl]-benzenamine

Using the procedure of Example 5, 5 g of the product of Example 6 and 25 ml of formic aldehyde and 10 g of powered zinc and 25 ml of acetic acid were reacted to obtain 2.7 g of N,N-dimethyl-3-[5-ethyl-4-(4-methoxyphenyl)-4H-1,2,4-triazol-3-yl]-benzenamine melting at 170° C.

EXAMPLE 8

3-propyl-4-(4-methoxyphenyl)-5-(4-nitrophenyl)-4H-1,2,4-triazole

STEP A:

2-[(4-methoxyphenyl)-imino-(4-nitrophenyl)-methyl]-hydrazide of butanoic acid 9.03 ml of triethylamine were added to a solution of 13.36 g of butanoic acid hydrazide (prepared as Step B of Example 1 for propionic acid hydrazide) in 760 ml of toluene and 19 g of N-(4-methoxyphenyl)-4-nitrobenzene carboximidoyl chloride (Step A of Example 1) were then added all at once. After standing for 30 minutes, the mixture was stirred for 65 hours at 20° C. By filtering, washing with toluene, triturating with water to eliminate triethylamine hydrochloride and drying under reduced pressure at 70° C., 19.2 g of 2-[(4-methoxyphenyl)-imino-(4-nitrophenyl)-methyl]hyrazide of butanoic acid melting at 155° C. were obtained.

STEP B:

3-propyl-4-(4-methoxyphenyl)-5-(4-nitrophenyl)-4H-1,2,4-triazole

A mixture of 19.2 of the product of Step A in 300 ml of toluene was refluxed for 1 hour and then cooled to ambient temperature and concentrated to dryness under reduced pressure to obtain 18 g of crude product which was crystallized from ethyl acetate. After separating and drying under reduced pressure at 70° C., 14.2 g of 3-propyl-4-(4-methoxyphenyl)-5-(4-nitrophenyl)-4H-1,2,4-triazole melting at 140° C. were obtained.

EXAMPLE 9

N,N-dimethyl-4-[4-(4-methoxyphenyl)-5-propyl-4H-1,2,4-triazol-3-yl]-benzenamine

Using the procedure of Example 5, 13 g of the product of Example 8, 25 g of powdered zinc, 65 ml of formic aldehyde and 65 ml of acetic acid were reacted to obtain 8.4 g of N,N-dimethyl-4-[4-(4-methoxyphenyl)-5-propyl-4H-1,2,4-triazol-3-yl]-benzenamine melting at 160° C.

EXAMPLE 10

5-[4-nitrophenyl]-4-(4-methoxyphenyl)-methyl-4H-1,2,4-triazol-3-methanol (L form)

STEP A: β-lactic acid hydrazide 9.7 ml of ethyl lactate (L form) were introduced slowly at 50° C. into 4.1 ml of hydrazine hydrate and after refluxing for 4 hours and evaporating under reduced pressure, a colorless oil was recovered which is utilized as is for the preparation for the next step.

STEP B:

3 ml of triethylamine were added at ambient temperature to a solution of 2 equivalents of -lactic acid hydrazide in 60 ml of toluene and then, 4.3 g of N-(4-methoxyphenyl)-4-nitrobenzene carboximidoyl chloride (Step A of Example 1) were added in two lots with stirring for 4 hours at ambient temperature. The mixture was then refluxed for 4 hours to obtain cyclization and the toluene was eliminated under reduced pressure. After washing with water, filtering and drying, 4.34 g of crude product were obtained which was purified by chromatography under pressure (eluent-chloroform-ethyl acetate-methanol: 47:50:3) to obtain 3 g of 5-[4-nitrophenyl]-4-(4-methoxyphenyl)-methyl-4H-1,2,4-triazol-3-methanol melting at 140° C.

EXAMPLE 11

5-[4-(dimethylamino)-phenyl]-4-(4-methoxyphenyl)-α-methyl-4H-1,2,4-triazol-3-methanol (L form)

Using the procedure of Example 5, 3 g of the product of Example 10, 6 g of powdered zinc, 15 ml of formic aldehyde and 15 ml of acetic acid were reacted to obtain 1.12 g of 5-[4-(dimethylamino)-phenyl]-4-(methoxyphenyl)-α-methyl-4H-1,2,4-triazol-3-methanol melting at 145° C.

Example 12

3-ethyl-4-(4-methoxyphenyl)-5-[4-(N,N-dimethylamino)-phenyl]-4H-1,2,4-triazole

STEP A: 4-dimethylamino-4-methoxybenzanilide 201 g of p-anisidine were added to a suspension of 300 g of 4-dimethylamino-benzoic acid chloride in 1200 ml of pyridine and the mixture was stirred until dissolution. Then, the mixture was refluxed for 3 hours and after cooling to ambient temperature, the reaction medium was poured into 6 liters of iced water. The precipitate was separated and washed with water, then dried under reduced pressure to obtain 423 g of 4-dimethylamino-4-methoxybenzanilide melting at 173° C.

STEP B:

Under argon and with stirring, 1 kg of 4-dimethylamino-4-methoxy-benzanilide, 8 liters of dichloromethane and 1130 ml of triethylamine were cooled to −40°±1° C. and, at this temperature, 2.6 liters of a solution of phosgene in toluene were introduced with stirring followed by re-heating to 20° C. over 2 hours. The solution was added to 40 liters of refluxing toluene and at the same time, a second solution of 489 g of propionic acid hydrazide in 489 ml of dichloromethane was added, all the while keeping the temperature of the reaction medium equal to or greater than 90° C. Distillation was maintained during the introduction of the two solutions at the end of the introduction, the volume distilled off was about 30 liters. The heating was stopped when the temperature of the reaction medium was equal to or greater than 100° C. The mixture was then cooled to 20° C. and washed successively with water, with water containing sodium hydroxide (4-1) and again with water. After extracting with dichloromethane, the extracts were dried and 100 g of active carbon were added followed by stirring and filtering. The filtrate was washed with dichloromethane and concentrated by distilling under atmospheric pressure down to a volume of 2 liters. The mixture was cooled to 20° C. and held for 16 hours with stirring and then was filtered. The product was washed with toluene and dried at 60° C. to obtain 98 4 g of crude product. 61.5 g of crude product were also recovered from the toluene mother liquors of crystallization.

Purification

A mixture of 1,045 g of the crude product in 4,182 ml of toluene was refluxed with stirring under nitrogen and then, over 15 minutes, 104.5 g of active carbon were added. Stirring at reflux was continued for 15 minutes, followed by filtering while hot and washing with refluxing toluene. After cooling to 20° C. and stirring for one night at 20° C., the mixture was filtered and washed with toluene and dried at 60° C. to obtain 862.6 g of 3-ethyl-4-(4-methoxyphenyl)-5-[4-(N,N-dimethylamino)-phenyl]-4H-1,2,4-triazole melting at 167° C.

EXAMPLE 13

3,4-bis-(4-methoxyphenyl)-5-ethyl-4H-1,2,4-triazole

STEP A: N-(4-methoxyphenyl)-4-methoxybenzene carboximidoyl chloride

Using the procedure of Step A of Example 1, 60 g of 4-methoxy-N-(4-methoxyphenyl)-benzene carbamide (prepared as in Step A of Example 1 melting at 205° C.), 120 ml of thionyl chloride and 120 ml of toluene were reacted to obtain 56.5 g of N-(4-methoxyphenyl)-4-methoxybenzene carboximidoyl chloride melting at 116° C.

STEP B:

3,4-bis-(4-methoxyphenyl)-5-ethyl-4H-1,2,4-triazole

Using the procedure of Step B, of Example 4, 3.46 g of the product of Step A, 2.21 g of propionic acid hydrazide, 1.74 ml of triethylamine and 50 ml of toluene were reacted to obtain 2.8 g of 3,4-bis-(4-methoxyphenyl)-5-ethyl-4H-1,2,4-triazole melting at 122° C.

EXAMPLE 14

5-[4-(dimethylamino)-phenyl]-4-(4-methoxyphenyl)-α-methyl-4H-1,2,4-triazol-3-methanol acetate (L form)

0.47 g of sodium hydride were added to a suspension of 3.3 g of the product of Example 11 in 33 ml of tetrahydrofuran and the mixture was stirred for 30 minutes. Then, 0.92 g of acetyl chloride were added, and the mixture was stirred for 16 hours under an inert atmosphere. After concentrating to dryness, the residue was taken up in 30 ml of water and the mixture was stirred for 30 minutes, and filtered. The product was washed with water and dried. After purifying by chromatography under pressure (eluent:ethyl acetate-chloroform 8-2), 2.8 g of 5-[4-(dimethylamino)-phenyl]-4-(4-methoxyphenyl)-α-methyl-4H-1,2,4-triazol-3-methanol acetate were obtained which when crystallized from toluene melted at 208° C. and had a specific rotation of $[\alpha]_D = -16° \pm 1°$ (c=1% chloroform).

Analysis: $C_{21}H_{24}N_4O_3$ molecular weight=380.450; Calculated: % C 66.30; % H 6.36; % N 14.73; Found: 66.0; 6.3; 14.6.

EXAMPLE 15

5-[4-dimethylamino)-phenyl]-4-(4-methoxyphenyl)-α-methyl-4H-1,2,4-triazol-3-methanol (DL form)

STEP A: Lactic acid hydrazide (DL form)

50 g of DL-methyl lactate and 24.2 g of hydrazide hydrate were heated for 4 hours 30 minutes at 100°/110° C. and the water was eliminated by entrainment with xylene to obtain lactic acid hydrazide in the form of an oil which was used as is for the next step.

Step B:

2.36 g of triethylamine were added to a suspension of 5 g of 4-dimethylamino-4-methoxy benzanilide (prepared as in Example 12) in 50 ml of methylene chloride and the mixture was cooled to −40° C. Then over 20 minutes and under an inert atmosphere, a solution of 5.75 ml of phosgene in toluene is added, and the mixture was re-heated to 20° C. over 90 minutes. The solution obtained was introduced into 200 ml of refluxing toluene and simultaneously a solution of 2.9 g of lactic acid hydrazide (DL form) in 6 ml of dimethylformamide was added. A part of the solvents was eliminated by distilling and then, after heating for 30 minutes to 107°–110° C., the reaction mixture was cooled and washed first with water, then with an N aqueous solution of sodium hydroxide and again with water. After extracting with methylene chloride and concentrating to dryness, 7.1 g of crude product were obtained which was crystallized from a mixture of ethyl acetylacetate and isopropyl ether (3–6) and then from pure ethyl acetate to obtain 5-[4-dimethylamino)phenyl]-4-(4-methoxyphenyl)-α-methyl-4H-1,2,4-triazol-3-methanol melting at 170° C.

Analysis: $C_{19}H_{22}N_4O_2$: molecular weight=338.413; Calculated: %C 67.43; %H 6.55; %N 16.55; Found: 67.2; 6.8; 16.3.

EXAMPLE 16

5-[4-(dimethylamino)-phenyl]-4-(4-methoxyphenyl)-α-methyl-4H-1,2,4-triazol-3-methanol (DL form)

Using the procedure of Example 14, 2.4 g of the product of Example 15, 0.336 g of sodium hydride and 0.660 g of acetyl chloride were reacted to obtain 2.24 g of 5-[4-(dimethylamino)-phenyl]-4-(4-methoxyphenyl)-α-methyl-4H-1,2,4-triazol-3-methanol which melted at 190° C. after it was crystallized from toluene.

Analysis: $C_{21}H_{24}N_4O_3$: molecular weight=380.450; Calculated: %C 66.3; %H 6.36; %N 14.73; Found: 66.4; 6.5; 14.8.

EXAMPLE 17

Pharmaceutical compositions

Tablets were prepared containing 50 mg of product of Example 11 and sufficient excipient of lactose, talc, starch, magnesium stearate for a tablet weight of 360 mg.

PHARMACOLOGICAL STUDY

A. Analgesic activity

The test employed is based on the method of Koster et al [Fed. Proc. 1959, Vol. 8, p. 412] wherein the intraperitoneal injection of acetic acid causes in mice repeated movements of stretching and twisting which can continue for more than six hours. Analgesics prevent or diminish the syndrome which can be considered as an external manifestation of a diffuse abdominal pain. A 1% solution of acetic acid in water was used and under these conditions, the dose releasing the syndrome was 0.01 ml/g, or 100 mg/kg of acetic acid. The products of Example 11 was administered orally half an hour before the injection of the acetic acid, the mice having fasted since the day before the test. The stretchings were observed and counted for each mouse during a 15 minutes observation period beginning immediately after the injection of the acetic acid. The results expressed as the $DA_{50}$ which is the dose which enables a diminution of 50% to be obtained in the number of stretchings by comparison with the control animals, was 4 mg/kg.

B. Anti-inflammatory activity: chronic arthritis with adjuvant (preventative treatment)

In a rat, the injection of an adjuvant of "Freund" type into a hind paw causes the rapid appearance of a primary inflammatory lesion in this paw, then, after a latency period of 13 to 15 days, the appearance of a secondary arthritis affecting in particular the other hind paw. This test was carried out on male rats aged from 42 to 50 days which received as an intraplantary injection, 0.1 ml of "Freund" type adjuvant (suspension in vaseline oil of 6 mg per ml of killed mycobacterium butyricum). The animals received the product of Example 11 orally from day 0 (day of injection of the adjuvant) until the day before they were killed which took place on day 17. Control arthritic animals and normal control animals received only the vehicle. The criteria by which the activity of the substances under study was determined were the increases in volume of the hind paws which were not injected (secondary inflammation) by comparison with the average volume of the corresponding paws of the normal controls. The $DA_{50}$ was determined which was the dose which reduced by 50% the increases in volume of the hind paws of the treated animals by comparison with the control animals and the result obtained showed notable activity of the product of Example 11 in this test.

Various modifications of the compounds and methods of the invention may be made without departing from the spirit or scope thereof and it should be understood that the invention is intended to be limited only as defined in the appended claims.

What we claim is:

1. A compound of the formula

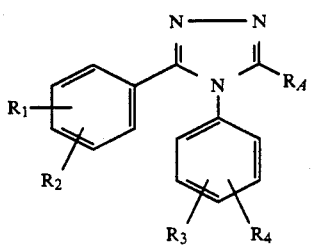

wherein $R_1$, $R_2$, $R_3$ and $R_4$ are in any position on the benzene nuclei and are individually selected from the group consisting of hydrogen, —OH, alkyl and alkoxy of 1 to 4 carbon atoms, —$NH_2$, —$CF_3$, halogen, —$NO_2$, —NH—$Alk^1$, and

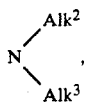

$Alk^1$, $Alk^2$, and $Alk^3$ being individually alkyl of 1 to 4 carbon atoms or $R_1$ and $R_2$ or $R_3$ and $R_4$ together form methylenedioxy and $R_A$ is selected from the group consisting of —CHOH—$Alk^4$ and

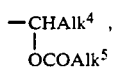

$Alk^4$ and $Alk^5$ individually being alkyl of 1 to 5 carbon atoms and their acid addition salts in racemic or optically active form.

2. The compound of claim 1 wherein one of $R_1$ and $R_2$ is hydrogen and the other is p-methoxy or p-dimethylamino.

3. The compound of claim 1 wherein one of $R_3$ and $R_4$ is hydrogen and the other is p-methoxy or p-dimethylamino.

4. The compound of claim 2 wherein one of $R_3$ and $R_4$ is hydrogen and the other is p-methylamino.

5. A compound of claim 1 selected from the group consisting of 5-[4-(dimethylamino)-phenyl]-4-(4-methoxyphenyl)-α-methyl-4H-1,2,3,4-triazol-3-methanol and its non-toxic, pharmaceutically acceptable acid addition salts in racemic or optically active form.

6. An analgesic composition comprising an analgesically effective amount of at least one compound of claim 1 and an inert pharmaceutical carrier.

7. The composition of claim 6 wherein one of $R_1$ and $R_2$ is hydrogen and the other is p-methoxy or p-dimethylamino.

8. The composition of claim 6 wherein one of $R_3$ and $R_4$ is hydrogen and the other is p-methoxy or p-dimethylamino.

9. The composition of claim 7 wherein one of $R_3$ and $R_4$ is hydrogen and the other is p-methoxy or p-dimethylamino.

10. The composition of claim 6 wherein the active compound is selected from the group consisting of 5-[4-(dimethylamino)-phenyl]-4-(4-methoxyphenyl)-α-methyl-4H-1,2,3,4-triazol)-3-methanol and its non-toxic, pharmaceutically acceptable acid addition salts in racemic or optically active form.

11. A method of relieving pain in warm-blooded animals comprising administering to warm-blooded animals an analgesically effective amount of at least one compound of claim 1.

12. The method of claim 11 wherein one of $R_1$ and $R_2$ is hydrogen and the other is p-methoxy or p-dimethylamino.

13. The method of claim 11 wherein one of $R_3$ and $R_4$ is hydrogen and the other is p-methoxy or p-dimethylamino.

14. The method of claim 12 wherein one of $R_3$ and $R_4$ is hydrogen and the other is p-methoxy or p-dimethylamino.

15. The method of claim 11 wherein the active compound is selected from the group consisting of 5-[4-(dimethylamino)-phenyl]-4-(4-methoxyphenyl)-α-methanol-4-H-1,2,3,4-triazol-3-methanol and its non-toxic, pharmaceutically acceptable acid addition salts in racemic or optically active form.

* * * * *